United States Patent [19]
Collier et al.

[11] Patent Number: 5,451,519
[45] Date of Patent: Sep. 19, 1995

[54] CLONING RESTRICTION ENDONUCLEASE GENES BY MODULATING METHYLTRANSFERASE ACTIVITY

[75] Inventors: Gordon B. Collier, Washington, D.C.; John F. Connaughton, Laytonsville; Jack G. Chirikjian, Potomac, both of Md.

[73] Assignee: Georgetown University, Washington, D.C.

[21] Appl. No.: 68,678

[22] Filed: May 28, 1993

[51] Int. Cl.$^6$ .................. C12N 9/22; C12N 15/55
[52] U.S. Cl. .................. 435/199; 435/252.33; 435/320.1; 435/193; 536/23.2
[58] Field of Search .............. 435/199, 193, 252.33; 435/320.1; 536/23.2

[56] References Cited

U.S. PATENT DOCUMENTS 5,098,839 3/1992 Polisson .................. 435/199
5,179,015 1/1993 Wilson et al. .................. 435/172.3

OTHER PUBLICATIONS

Lunnen, K. D., et al. (1988) Gene 74, 25–32.
Wilson, G. G. (1988) Gene 74, 281–289.
Wilson, G. G. (1988) TIG 4(11), 314–318.
Piekarowicz, A., et al. (1991) Nuc. Acids Res 19(8), 1831–1835.
Roberts, "Restriction Enzymes And Their Isoschizomers", *Nucleic Acis Research*, vol. 18:2331–2365.
Mann et al.,"Cloning Of Restriction And Modification Genes In *E. Coli:* The HhaII System From *Haemophilus Haemolyticus*", *Gene*, vol. 3:97–112, (1978).
Wilson, "Organization Of Restriction-Modification Systems", *Nucleic Acids Research*, vol. 19:2539–2566. (1991).
Takiff et al., "Genetic Analysis Of The *rnc* Operon Of *Escherichia coli*", *Journal of Bacteriology*, vol. 171:2581–2590, (1989).
C. Satishchandran et al., "Novel *Escherichia coli* K–12 Mutants Impaired In S–Adenosylmethionine Synthesis", *Journal Of Bacteriology*, vol. 172:4489–4496, (1990).
Rose, "The Nucleotide Sequence Of pACYC184", *Nucleic Acids Research*, vol. 16:355, (1988).
Landoulsi et al., "The *E. coli* Cell Surface Specifically Prevents The Initiation of DNA Replication At oriC On Hemimethylated DNA Templates", *Cell*, vol. 63:1053–1060, (1990).
Russell et al., "Hemimethylation Prevents DNA Replication In *E. coli*", *Cell*, vol. 50:1071–1079, (1987).
Lewis et al., "Isolation Of DNA Damage-Inducible Promoters In *Escherichia coli:* Regulation Of polB (dinA), dinG, and dinH by LexA Repressor", *Journal of Bacteriology*, vol. 174:3377–3385, (1992).
Raymond-Denise et al., "Identification Of dinR, A DNA Damage-Inducible Regulator Gene Of *Bacillus Subtilis*", *Journal of Bacteriology*, vol. 173:7084–7091, (1991).
Abramic et al., "Purifaction Of An Ultraviolet-Inducible, Damage-Specific DNA-Binding Protein From Primate Cells", *The Journal of Biological Chemisty*, vol. 266:22493–22500, (1991).

(List continued on next page.)

*Primary Examiner*—Charles L. Patterson, Jr.
*Attorney, Agent, or Firm*—Foley & Lardner

[57] ABSTRACT

The present invention relates to a method for cloning genes that encode restriction endonucleases by altering the level of a methyl donor co-factor of a DNA methyltransferase that protects the DNA of a host cell from damage by a restriction endonuclease. The method can be used to screen entire DNA libraries en masse to identify clones that encode restriction enzymes by growing one library replicate under high or normal methyl donor conditions to protect host DNA and a second library replicate under low methyl donor conditions allowing DNA damage from the active restriction endonuclease. Clones that encode a restriction enzyme are identified by decreased growth or color produced in response to double stranded DNA damage under the low methyl donor conditions. Colorimetric methods useful in the invention can use SOS-sensitive promoters operably linked to β-galactosidase, which detect DNA damage.

40 Claims, 5 Drawing Sheets

OTHER PUBLICATIONS

Sebastian et al., "A Damage-Responsive DNA Binding Protein Regulates Transcription Of The Yeast DNA Repair Gene PHR1", *Proc. Natl. Acad. Sci. USA*, vol. 88:11251-11255, (1991).

Raymond-Denise et al., "Expression Of The *Bacillus subtilis dinR and recA* Genes After DNA Damage and During Competence", *Journal of Bacterilogy*, vol. 174:3171-3176, (1992).

Siede et al., "Regulation Of The Yeast RAD2 Gene: DNA Damage-Dependent Induction Correlates With Protein Binding To Regulatory Sequences And Their Deletion Influences Survival", *Mol Gen Genet*, vol. 232:247-256, (1992).

Chao, "Damage-Recognition Proteins As A Potential Indicator Of DNA-Damage-Mediated Sensitivity Or Resistance Of Human Cells To Ultraviolet Radiation", *Biochem. J.*, vol. 282:203-207, (1992).

Luethy et al., "Activation Of The gadd153 Promoter By Genotoxic Agents: A Rapid And Specific Response To DNA Damage", *Cancer Research*, vol. 52:5-10, (1992).

Petit et al., "Characterization Of *din Y*, a New *Escherichia coli* DNA Repair Gene Whose Products Are Damage Inducible Even in a lex(Def) Background", *Journal of Bacteriology*, vol. 175:642-646, (1993).

Hafner et al., "Isolation Of A metK Mutant With A Temperature-Sensitive S-Adenosylmethionine Synthetase", *Journal of Bacterilolgy*, vol. 132:832-840, (1977).

Piekarowicz et al., "Isolation Of Temperature-Sensitive McrA and McrB Mutations An Complementation Analysis Of The McrBC Region Of *Escherichia coli* K-12", *Journal of Bacterilogy*, vol. 173:150-155, (1991).

Heitman et al., "SOS Induction As An In Vivo Assay Of Enzyme-DNA Interactions", *Gene*, vol. 103:1-9, (1991).

Hughes et al., "Expression Of The Cloned Coliphage T3 S-Adenosylmethionine Hydrolase Gene Inhibits DNA Methylation And Polyamine Biosynthesis in *Escherichia coli*", *Journal of Bacterilolgy*, vol. 169:3625-3632, (1987).

Hughes et al., "Nucleotide Sequence And Analysis Of The Coliphage T3 S-Adenosylmethionine Hydrolase Gene And Its Surrounding Ribonuclease III Processing Sites", *Nucleic Acids Research*, vol. 15:717-729, (1987).

Little et al., "The SOS Regulatory System Of *Escherichia coli*", *Cell*, vol. 29:11-22, (1982).

Porter et al., "Growth Inhibition By Methionine Analog Inhibitros Of S-Adenosylethionine Biosynthesis In The Absence Of Polyamine Depletion", *Biochemical and Biophysical Research Communications*, vol. 122:350-357, (1984).

Sufrin et al., "A Potent Inhibitor Of The Enzymatic Synthesis Of S-Adenosylmethionine", *Biochemical and Biophysical Research Communications*, vol. 106:251-255, (1982).

Piekarowicz et al., "Construction Of A Temperature-Sensitive Mutation For The Direct Identification Of Plasmids Encoding DNA Methyltransferases", *Gene*, vol. 74:233-235, (1988).

Mead et al., "Single-Stranded DNA 'blue' T7 Promoter Plasmids: A Versatile Tandem Promoter System For Cloning And Protein Engineering", *Protein Engineering*, vol. 1:67-74, (1986).

Walder et al., "Cloning Of The MspI Modification Enzyme", *The Journal of Biological Chemistry*, vol. 258:1235-1241, (1983).

Brooks et al., "Cloning and Characterization of the BanHI Restriction Modification System", *Gene*, vol. 74:13, (1988).

Howard et al., "Cloning the DdeI Restriction-Modification System Using A Two-Step Method", *Nucleic Acids Research*, vol. 14:7939-7951, (1986).

Nwankwo et al., "Cloning Of Two Type II Methylase Genes That Recognise Asymmetric Nucleotide Sequences:FokI and HgaI", *Mol Gen Genet*, vol. 209:570-574, (1987).

Borck et al., "The Construction In Vitro of Transducing Derivatives of Phage Lambda", *Molec. Gen. Genet.*, vol. 146:199-207, (1976).

Kessler et al., "Specificity Of Restriction Endonucleases And DNA Modification Methyltransferases—A Review (Edition 3)", *Gene*, vol. 92:1-248, (1990).

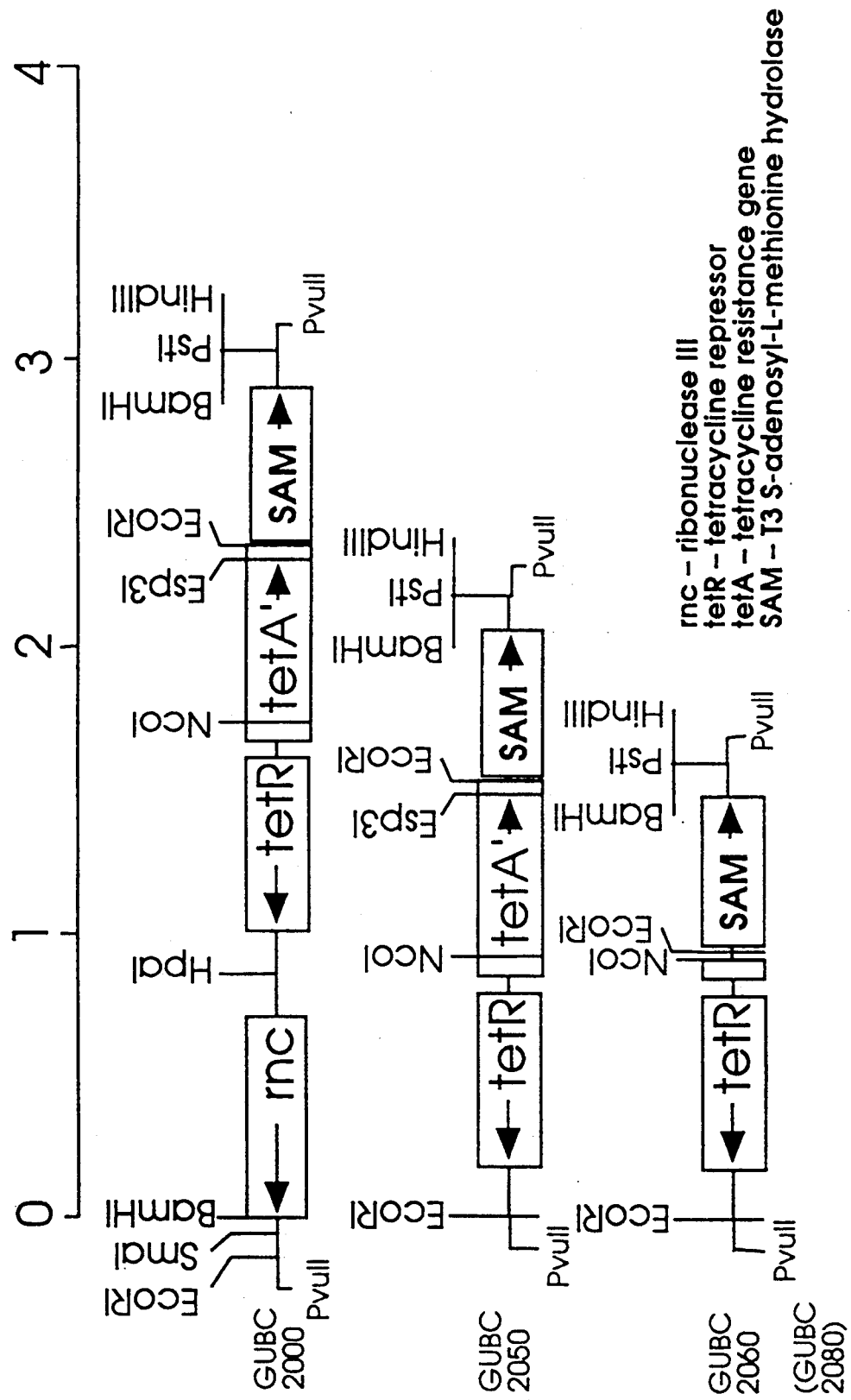

CLONING RESTRICTION ENDONUCLEASE GENES BY MODULATING METHYLTRANSFERASE ACTIVITY

BACKGROUND OF THE INVENTION

The present invention relates to identifying and isolating genes that encode restriction endonucleases and genes that encode methyltransferases.

Restriction endonucleases originally were identified by studying the inability of bacteriophage from strains of *E. coli* to infect other strains of E. coli. (Dussoix and Arber, *J. Mol. Biol.* 5: 37 (1962)). It now is well established that this phenomena, called restriction, is mediated by two types of enzymes, which are called restriction endonucleases and DNA methyltransferases.

Restriction endonucleases primarily cleave double-stranded DNA. Methyltransferases transfer a methyl group from a methyl donor co-factor such as S-adenosyl-L-methionine to a purine or pyrimidine primarily in double-stranded DNA. Methylation by the methyltransferase prevents cleavage of the DNA by the cognate restriction endonuclease. Endogenous DNA of the organism thus is protected by the methyltransferase from damage by the restriction endonuclease. Exogenous DNA entering the cell, which has not been exposed to the methyltransferase, is generally not properly modified and is degraded by the restriction endonuclease.

The two types of enzymes working together function as a simple immune system. The methyltransferase "marks" endogenous DNA as "self" by a sequence-specific pattern of methylation that renders the DNA "immune" to cleavage by the endonuclease. DNA that is not properly modified is seen as "non-self," at least in the sense that it is degraded by the restriction enzyme. Thus, the two cognate enzymes provide a simple mechanism of protecting against the effects of an invading DNA.

In general, methyltransferases and restriction endonucleases form cognate pairs that recognize the same short sequence of DNA with exquisite specificity and require this recognition sequence for activity. Self:non-self recognition in restriction derives from this property of the enzymes. Endogenous methyltransferases modify their genomic DNA at the recognition sites of the cognate restriction endonuclease, protecting it from the endonuclease. The enzymes in different organisms recognize different DNA sequences. Therefore, the methyltransferase from one organism will not protect DNA against the restriction endonuclease from another organism. Sequence specificity allows a single enzymatic mechanism to insulate interacting organisms against the deleterious effects of exogenous DNAs that may be carried between them by vectors or incorporated from the environment. The same sequence specificity is crucial to the practical importance of the enzymes in biotechnology.

The sequences recognized by restriction endonucleases and methyltransferases most often are four or six bases long and centrally symmetric. There are many variations on this basic theme, however, and many five and eight base pair recognition sequences are known, as well as asymmetric recognition sequences and recognition sequences that are located remotely from the modification or cleavage site.

Restriction endonucleases provide the only practical means to cut DNA in a reproducible fashion. Thus, the enzymes have become essential tools in the procedures for isolating, characterizing, studying and expressing genes. In addition, the enzymes now are widely used in clinical and forensic applications in analytic techniques that depend on restriction fragment length polymorphisms. It is likely that the use of these enzymes will increase in the future in both the research setting and commercially as molecular biology research continues its acceleration into marketplace applications. Laboratory and commercial endeavors both will demand variety in the properties of commercially available restriction endonucleases and methyltransferases, which will increase flexibility in using these reagents.

Fortunately, the prokaryotes have evolved a remarkable variety in these enzymes, particularly in their recognition sequences. Two recent compilations list about 1500 restriction endonucleases that have been identified. See Roberts, R, *Nuc. Acids Res.* 18 Supp: 2331 (1990) and Kessler et al., *Gene* 92: 1 (1990), both of which are herein incorporated by reference in their entirety. However, only about 200 of the 1500 cataloged restriction endonucleases are readily available through commercial channels.

The limited availability of the enzymes is attributable largely to difficulties producing the enzymes from many organisms and to the shortcomings of alternative production techniques that depend on gene cloning and expression.

Difficulties associated with purifying enzymes from the natural host range from safety problems to low yields. For instance, a variety of organisms that produce potentially useful restriction endonucleases and methyltransferases are human pathogens. Culturing these organisms to purify the enzymes poses a risk to human health that interferes with commercial manufacture.

Even when safety is not a concern, the natural sources of many restriction enzymes cannot provide economical yields. Some potential sources of the enzymes grow only under exotic conditions. Others simply grow very poorly. Still others produce vanishingly small amounts of the enzymes. Even when the growth characteristics of an organism are favorable, it often is difficult to purify the restriction enzymes, due to protease activities or contaminants that are hard to remove, for instance. Another complication of this type occurs in trying to purify the enzymes from organisms that produce several restriction endonucleases. *Haemophilus aegyptius* produces three restriction endonucleases, for instance.

Several techniques have been developed to overcome the limitations imposed on enzyme production by disadvantageous properties of a natural host. Universally, these methods involve cloning genes that encode restriction endonucleases and methyltransferases and then expressing the genes in a host having properties suitable to enzyme production and purification. Wilson (1988) and Lunnen (1988) have reviewed these methods in some detail. (Wilson et al., *Gene*, 74: 281 (1988) and Lunnen et al., *Gene* 74: 25 (1988), both herein incorporated by reference in their entirety). Nonetheless, as discussed below, no universally practical method has yet been developed to clone these genes.

Conventional cloning techniques have been used to clone genes that encode restriction endonucleases and methyltransferases, with some success. As a general rule, these techniques require an effective probe to fish the desired gene out of a genomic or cDNA library.

Relatively large amounts of enzyme and considerable investment, effort, expertise and time are required to develop effective immunological or hybridization probes for these genes. Conventional cloning strategies therefore have been used to clone only a few restriction enzymes of manifest economic or scientific interest.

A number of procedures designed specifically to clone genes that encode restriction enzymes have been developed to overcome the problems associated with conventional cloning techniques that require large amounts of protein and immunological reagents or sequence information.

In one technique of this type, DNA (or, potentially, cDNA) from the natural source of the enzyme is shotgun cloned and expressed in recombinant host cells. The cells are screened by exposing them en masse to infection by a bacteriophage, i.e. by restriction. Cells that express a restriction endonuclease should survive the infection and proliferate. This strategy was used to clone the restriction endonucleases HhaII and PstI, as described, respectively, in Mann et al., Gene 3: 97 (1979) and Walder et al., Proc. Nat'l Acad. Sci. USA 78: 1503 (1981).

This strategy suffers from several disadvantages that prevent it from serving as a generally effective method for isolating genes that encode restriction endonucleases and methyltransferases. For one thing, selection by restriction is "leaky," resulting in a high background of false positives. In addition, a resistance to bacteriophage infection is not mediated exclusively by the presence of a cloned restriction endonuclease but can arise from a variety of other factors. A variety of host cell mutations, for instance, can confer resistance, as described in Nwanko et al., Mol. Gen. Genet., 209: 570 (1988). Thus, the method provides only a collection of DNAs which must be characterized further to identify any cloned methyltransferases or restriction endonuclease gene that may be present among them.

An indirect strategy has been developed for cloning restriction endonuclease genes by a methylation protection assay. This technique utilizes in vitro digestion to select DNA encoding a methyltransferase. Since genes that encode a cognate restriction endonuclease and methyltransferase generally are closely linked in the natural host, cloned DNA fragments that express a methyltransferase usually also encode at least a part of the cognate methyltransferase. (Linkage of cognate restriction endonuclease and methyltransferase genes is discussed in Wilson, Nuc. Acids Res. 19: 2539 (1991)).

In carrying out the strategy, DNA from the natural source of the restriction enzyme is shotgun cloned and expressed in a suitable host. The cloned DNA is reisolated from the host cells, pooled and digested in vitro by the restriction endonuclease of interest. The restricted DNA then is transformed into a host and cultured. At best, the only cloned DNAs that will be viable after in vitro restriction endonuclease digestion will be those that expressed the cognate methyltransferase in the transformed host cells. Thus, colonies that arise from the in vitro restriction products should encode the methyltransferase and at least a portion of the linked restriction endonuclease. The procedure originally was described by Borck et al., Mol. Gen. Genet. 146: 199 (1976) and used to clone the gene encoding the hsdRSM$_k$ endonuclease.

The procedure suffers from several drawbacks, however. First, DNAs that do not contain a restriction site recognized by the endonuclease in the in vitro digestion will not be inactivated. Four base pair recognition sequences are likely to be present in almost all DNAs but the false positive background from siteless DNA increases with the length of the endonuclease recognition site.

In addition, not all cognate pairs of restriction endonucleases and methyltransferases are closely linked, and even closely linked genes may be separated during shotgun cloning. Thus, many times clones will encode the methyltransferase but not the restriction endonuclease.

Finally, methyltransferase expression often will not be adequate to protect the heterologous host against the restriction endonuclease. The adverse affect of the restriction enzyme on these cells in many cases will eliminate them from the population before they form discernable colonies. In this event, the method will not be useful for cloning the restriction endonuclease.

Another technique for cloning genes that encode restriction endonucleases is designed to avoid the difficulties that occur when expression of a cloned methyltransferase is not adequate to protect the host against the deleterious effects of the cognate restriction endonuclease. One version of this approach is to shotgun clone DNA from the source organism into a protected host and then screen individual colonies for expression of the endonuclease. The method generally involves transforming a host to express a methyltransferase adequately to protect the host chromosomal DNA against the cloned restriction endonuclease. DNA from the source organism is shotgun cloned into the protected host. Clones that contain the restriction endonuclease gene are identified by screening crude extracts of colonies from the shotgun library for endonuclease activity in vitro in DNA digestion assays. The technique has been used to clone genes that encode the BamHI and DdeI restriction endonucleases, as described by Brooks et al., Gene 74: 13 (1988) and Howard et al., Nuc. Acids Res. 14: 7939 (1986), respectively.

In a modification of this technique, a heterologous methyltransferase gene is used to protect the host cell DNA from nucleolytic attack by the cloned restriction endonuclease. In this approach, a non-cognate methyltransferase gene is expressed in the host before introduction of the shotgun cloned DNA from the source organism. The technique has been used to clone the genes that encode the restriction endonucleases FspI and HaeIII, as described in Wilson and Meda, U.S. Pat. No. 5,179,015.

Both methods suffer from two significant disadvantages, among others. First, a gene encoding a protecting methyltransferase must be available or must be separately obtained to construct a protected host. Furthermore, only individual colonies or small pools of colonies can be screened in this approach for the presence of in vitro restriction endonuclease activity. Thus, the approach cannot be applied where a suitable methyltransferase gene cannot be obtained. Moreover, it is very laborious even when a suitable host expressing the methyltransferase activity is available. It's use therefore has been limited.

Finally, genes that encode restriction endonucleases can be cloned using a temperature sensitive restriction endonuclease that cleaves methylated DNA, as described in Piekarowicz et al., Gene 74: 233 (1988) and Piekarowicz et al., J. Bac. 173: 150 (1991). According to this method, a shotgun library of DNA from the natural source of a restriction enzyme is transformed under permissive conditions into a host that is temperature sensitive for a methylation-dependent endonuclease. After growth under permissive conditions replicates are shifted to non-permissive conditions. DNA in cells that express a cloned methyltransferase will be methylated and will be adversely affected by the activity of the methylation dependent endonuclease.

The method has been demonstrated only in a model system. In this example, a clone encoding the HaeIII methyltransferase was introduced into an *E. coli* host temperature sensitive for mcrB, a methylation dependent endonuclease of the *E. coli* mcr restriction system. (The E. coli mcr and mrr digest DNA methylated at specific sequences, as described in Raleigh et al., *Proc. Nat'l. Acad. Sci.*, 83: 9070 (1986) and Dila et al., *J. Bac.* 172: 4888 (1990)). Transformed host cells were grown initially under permissive conditions at 42° C., where mcrB is inactive, providing for expression of the HaeIII methyltransferase and resultant methylation of the host DNA. Then, replicates were grown at the non-permissive temperature, 30° C., where mcrB is active. Under non-permissive conditions at 30° C., the mcrB endonuclease degraded host DNA methylated by the HaeIII methyltransferase causing the death of cells that expressed this gene. The method suffers from the drawbacks of other methods that select for the methyltransferase.

In sum, there is great interest in restriction endonucleases and methyltransferases. They are employed widely in research and in commercial applications. Cloning the genes that encode these enzymes is key to increasing the variety, quality and economy of commercially available restriction endonucleases and methyltransferases. Producing the enzymes by expressing these genes in a heterologous host offers considerable practical advantages. It avoids the safety problems posed by pathogenic sources of useful enzymes. It circumvents disadvantageous growth habits of the natural host. It vitiates endogenous factors that cause low yields from the natural source. Furthermore, standard expression systems offer significant advantages in reliability, batch to batch uniformity, and economy. Production by cloned genes promises to expand the variety and improve the specific activity, concentration, purity and overall quality of restriction endonucleases and methyltransferases available in the marketplace. Thus, there is a continuing need for improved methods to identify and isolate genes that encode these enzymes.

SUMMARY OF THE INVENTION

It is therefore an object of the present invention to provide methods for cloning genes that encode restriction endonucleases and genes that encode methyltransferases by modulating the activity of a methyl donor cofactor of a methyltransferase.

It is another object of the present invention to provide vectors useful in cloning genes that encode restriction endonucleases and genes that encode methyltransferases.

It is yet another object of the invention to provide host cells useful in cloning genes that encode restriction endonucleases.

In accordance with the foregoing objects, there has been provided a method for cloning a gene encoding a restriction endonuclease comprising the step of modulating the cellular concentration of a methyl donor cofactor of a methyltransferase to detect the presence of the restriction endonuclease encoded by the cloned gene.

In one aspect of the invention there is provided a method for cloning a gene encoding a restriction endonuclease in which cellular DNA is protected from cleavage by the restriction endonuclease under a first growth condition and cellular DNA is cleaved detectably under a second growth condition.

In another aspect of the invention there is provided a method comprising: (a) introducing cloned DNAs comprising a gene for a restriction endonuclease into a cellular host; (b) propagating host cells in a replicable format under a first growth condition, then; (c)propagating a replicate of the host cells of step (b) under a second growth condition, and (d) detecting DNA encoding the gene by an effect of the gene that differs between the first and the second growth conditions.

In a preferred embodiment of this aspect of the invention DNA encoding a restriction endonuclease is determined by comparing cell growth under first and second growth conditions and decreased growth under second growth conditions indicates cells that contain the DNA encoding the restriction endonuclease.

In another preferred embodiment of this aspect of the invention a DNA cleavage-dependent transcription regulatory region controls expression of a detectable activity and DNA encoding a restriction endonuclease gene is detected by the DNA cleavage-mediated induction or repression of the detectable activity.

In a particularly preferred embodiment of the foregoing aspect of the invention the transcription regulatory region is a transcription regulatory region of an SOS responsive gene. Especially preferred SOS responsive genes in this aspect of the invention are the dinA, dinB, dinD, dinF, dinG, dinH, dinR, dinY, DDB, DRP, gadd153, PHR1, RAD2 genes. In this aspect of the invention the promoter of the dinD gene is a very highly preferred embodiment. dinA, dinB, dinD, dinF, dinG, dinH, dinR, dinY, DDB, DRP, gadd153, PHR1, RAD2 genes are described, for instance, in Little et al., *Cell* 29: 11 (1982), Lewis et al., *J. Bac.* 174: 3377 (1992), Petit et al., *J. Bac.* 175: 642 (1993), Luethy et al., *Cancer Res.* 52: 5 (1992), Abramie et al., *J. Biol. Chem.* 266: 22493 (1991), Raymond-Denise et al., *J. Bac.* 173: 7084 (1991), Chao et al., *Biochem. J.* 282: 203 (1992), Seide et al., *Mol. Gen. Genet.* 232: 247 (1992), Raymond-Denise et al., *J. Bac.* 174: 3171 (1992) and Sebastian et al., *Proc. Nat'l Acad. Sci.*, U.S.A. 88: 11251 (1991) which are herein incorporated by reference in their entirety.

In additional preferred embodiments of this aspect of the invention the DNA damage sensitive promoters express a reporter gene. In preferred embodiments of this aspect of the invention the reporter gene encodes a β-galactosidase, a cellulase, a luciferase, an alkaline phosphatase, a B-glucuronidase, a glutathionine S-transferase or chloramphenicol acetyltransferase. β-galactosidase, is particularly preferred in this aspect of the invention.

In accordance with still another aspect of the claimed invention there are provided host cells for detecting DNA damage. In a preferred embodiment of this aspect of the invention the host cells do not efficiently repair DNA damage by a restriction endonuclease. Highly preferred embodiments in this aspect of the invention are DNA ligase deficient cells. Particularly preferred cells are *E. coli* cells that are lig4, lig7 or lig4 and lig7 deficient cells.

In another embodiment of this aspect of the invention there are provided host cells that do not express a restriction-modification system that degrades methylated DNA. Preferred E. coli hosts in this aspect of the invention are mcrA, mcrB, mcrC, mcrD, mcrE, mcrF or mrr deficient.

In another aspect of the invention preferred hosts stably incorporate an exogenous DNA that encodes a DNA methyltransferase operably linked to a transcription regulatory region whereby the methyltransferase expression in the cells is effective to protect the DNA of the cells from nucleolytic degradation by the restriction endonuclease. In particularly preferred embodiments of this aspect of the invention the DNA methyltransferase and the restriction endonuclease are a homologous, cognate pair.

In another aspect of the invention methyl donor cofactors for altering the activity of a methyltransferase in a host are provided. Preferred methyl donor cofactors in this aspect of the invention are S-adenosyl-L-methionine and methylcobalamin. S-adenosyl-L-methionine is a particularly highly preferred methyl donor cofactor in this regard.

In yet another aspect, the invention provides means for controlling the cellular concentration of the methyl donor cofactor. In preferred embodiments of this aspect of the invention, the methyl donor cofactor is S-adenosyl-L-methionine and the cellular concentration of S-adenosyl-L-methionine is controlled by the activity of an enzyme for S-adenosyl-L-methionine synthesis or degradation. In certain preferred embodiments of this aspect of the invention the enzymes are S-adenosyl-L-methionine hydrolase, S-adenosyl-L-methionine decarboxylase or S-adenosyl-L-methionine methylthioadenosine-lyase. Among these embodiments the bacteriophage T3 S-adenosyl-L-methionine hydrolase is particularly preferred.

In a further aspect, the invention provides a means to modulate the activity of enzymes to control the cellular concentration of the methyl donor cofactor. Preferred embodiments of this aspect of the invention for regulating enzyme activity include temperature sensitive enzymes, enzyme inhibitors, and operably linking a gene encoding the enzyme to an inducible promoter.

In a preferred embodiment of this aspect of the invention, L-2-amino-4-methoxy-cis-BUT-3-ENOIC acid, selenomethionine, cycloleucine or 2-aminobicyclo[2.1.1]hexane-2-carboxylic acid is used to inhibit the activity of S-adenosyl-L-methionine synthetase activity.

In highly preferred embodiments of this aspect of the invention the expression in host cells of an exogenously derived gene encoding S-adenosyl-L-methionine hydrolase, S-adenosyl-L-methionine decarboxylase or S-adenosyl-L-methionine methylthioadenosine-lyase is controlled by an inducible promoter. A highly preferred inducible promoter in this aspect of the invention is the TN10 tetracycline promotor and the TN10 tetracycline repressor. In an especially preferred embodiment of this aspect of the invention the TN10 tetracycline promoter controls expression of bacteriophage T3 S-adenosyl-L-methionine hydrolase.

In a further aspect of the invention there is provided host cells that comprise (A) a first exogenously-derived inducible promoter not controlled by the cellular effects of DNA damage operably linked to a first exogenously-derived gene that encodes a protein for modulating the intracellular concentration of S-adenosyl-L-methionine, and (B) a second exogenously-derived promoter which is regulated by the cellular effects of restriction endonuclease-mediated DNA damage operably linked to a second exogenously-derived gene that encodes a reporter protein, wherein (C) inducing the first promoter modulates the intracellular concentration of S-adenosyl-L-methionine and restriction endonuclease-mediated DNA damage is determined by the reporter protein. A very highly preferred host for use in this aspect of the invention is E. coli GUBCE-1.

In yet a further aspect of the invention there is provided vectors for propagating DNA in a host cell which comprise an inducible promoter which is not controlled by the cellular effects of DNA damage operably linked to an exogenously derived gene that encodes a protein for modulating the intracellular concentration of S-adenosyl-L-methionine. A highly preferred embodiment of this aspect of the invention is the pGUBC-2080.

In yet another aspect of the invention there is provided isolated, purified DNA comprising a region encoding a cognate methyltransferase and restriction endonuclease obtained by a method comprising the step of modulating the cellular concentration of a methyl donor cofactor of a methyltransferase to detect the presence of an exogenously derived DNA encoding said restriction endonuclease in a host. In certain highly preferred embodiments of this aspect of the invention isolated, purified DNA is obtained by a method in which the concentration of S-adenosyl-L-methionine is controlled by chlortetracycline induced expression of a bacteriophage T3 S-adenosyl-L-methionine hydrolase gene operably linked to a TN10 tetracycline promoter and the presence of a gene encoding a restriction endonuclease is determined by SOS-induced expression of a β-galactosidase gene operably linked to the E. coli dinD1 promoter.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 2 is a diagram showing the construction of the plasmid pGUBC-2080. The diagram shows the PvuII tetR-SAM fragment which was inserted into the EcoRV site of pACYC184 to form pGUBC-2080. The diagram also shows that the TN10 tetA promotor-operator in the plasmid is operably linked to the bacteriophage T3 S-adenosyl-L-methionine hydrolase gene. Hydrolase expression by the plasmid can be repressed by the TN10 tetR repressor and derepressed by inducers of the repressor such as chlortetracycline.

DETAILED DESCRIPTION OF THE INVENTION

Figure 1A:
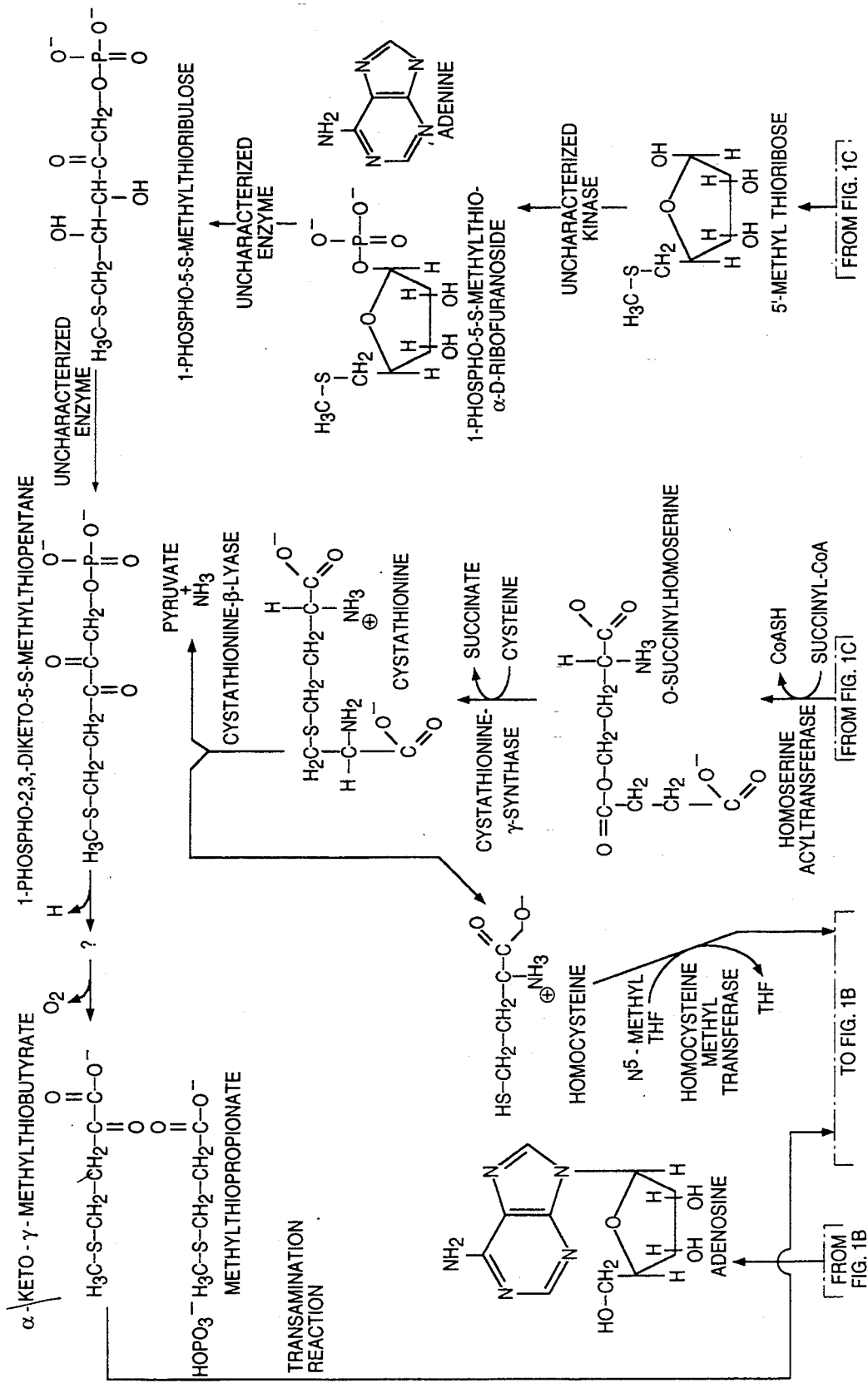
FIGS. 1A 1B and 1C are charts of S-adenosyl-L-methionine metabolism and utilization. The chart highlights enzymes that affect the cellular concentration of S-adenosyl-L-methionine in a cell.

Notwithstanding past failures to develop highly effective methods to clone genes that encode restriction endonucleases and genes that encode methyltransferases, it has been discovered that these genes can be cloned by modulating the intracellular concentration of a methyl donor co-factor of a methyltransferase.

In accordance with the present invention DNA from an organism that produces a restriction-modification enzyme of interest is shotgun cloned into a vector and expressed in a host characterized in that the intracellular concentration of a methyl donor co-factor of a methyltransferase in the host can be controlled by the conditions of growth. Under conditions for high concentrations of the methyl donor co-factor, cellular DNA is protected from the activity of a restriction endonuclease encoded by the cloned DNA. Under conditions for low concentrations of the methyl donor co-factor, cellular DNA is damaged by the activity of a restriction enzyme encoded by the cloned DNA. In accordance with the present invention clones in the shotgun library that contain DNAs of the source organism that encode a restriction enzyme are identified by detecting an increase in DNA damage under conditions for low concentration of the methyl donor cofactor.

Sources of DNA Encoding Restriction Enzymes

The invention is not limited to only certain sources of DNA. Any organism that produces a restriction endonuclease is a source of DNA for use in the invention. Any organism that produces a methyltransferase likewise is a source of DNA for use in the invention. In fact, any DNA that encodes a restriction endonuclease or a methyltransferase may be used as a source of DNA in accordance with the present invention.

For instance, as noted hereinabove, approximately 1500 restriction endonucleases were identified in recent lists that were published by Roberts, R, *Nuc. Acids Res.* 18 Supp: 2331 (1990) and Kessler et al., *Gene* 92: 1 (1990). All the organisms that produce a restriction endonuclease or methyltransferase in the lists are sources of DNA for use in the present invention.

New enzymes constantly are being discovered and the lists are constantly changing to incorporate new restriction endonucleases and methyltransferases. The sources of any newly discovered enzymes also may be used as sources of DNA for use in the invention.

Nor is the invention limited to a particular form of nucleic acid. Cloning in accordance with the invention can utilize any nucleic acid that may encode a restriction endonuclease or methyltransferase from the above-mentioned sources. Genomic DNA and messenger RNA both can be used in the invention using standard and well-known methods for making and using genomic and cDNA libraries. Moreover, genomic DNA, DNAs from organelle, episomal DNAs, and viral DNAs, inter alia, all may be used in the invention. In fact, the invention extends to any nucleic acid for cloning that may encode a restriction endonuclease or methyltransferase.

Genomic DNA is preferred in the invention for cloning restriction endonucleases or methyltransferases from prokaryotes. Primarily, the cognate restriction endonuclease and methyltransferase genes in prokaryotes are tightly linked. In general, therefore, the two genes will be cloned together and expressed together in the host cell. Similar facility of obtaining the two genes together by cDNA cloning is possible only for polycistronic mRNAs that encode both enzymes. In addition, prokaryotic genes do not contain introns and therefore can be expressed directly. And, since prokaryotic promoters often are quite active in heterologous hosts, it often will be possible to use the endogenous promoters of the restriction endonuclease and methyltransferase genes in the genomic fragment for expression in a transformed host.

Cloning DNA From the Source Organism

Methods suitable for use in the invention for obtaining, cloning and expressing nucleic acids from practically any organism are described in many widely available laboratory manuals and are well known to those of skill in the art. For instance, such methods are set forth in Sambrook et al., MOLECULAR CLONING: A LABORATORY MANUAL, 2ND Ed., Cold Spring Harbor Laboratory Press, Cold Spring Harbor, N.Y. (1989), the entirety of which is herein incorporated by reference.

Those of skill in the art will appreciate that a wide variety of cloning vectors can be used in the invention, including but not limited to bacteriophage-derived vectors, vectors derived from extrachromosomal genetic factor, e.g., plasmids, F factors, artificial chromosome vectors such as YACs, or any other autonomously replicating DNA. A wide variety of vectors that can be used in the invention are widely available and well known to those of skill in the art. Many such vectors are described, for instance, in Sambrook (1980), supra.

Likewise, methods for introducing DNAs into hosts for use in the invention are described in many laboratory manuals and are well known to those of skill in the art. Thus, DNA from a source organism ligated into a vector can be introduced into a suitable host by well-known methods of transformation, transfection, electroporation and ballistic propulsion, to name the most commonly used methods. Methods of these types suitable for use in the invention are described in Sambrook (1989), supra.

Hosts, Methyl Donor Co-factors and Methods for Modulating the Intracellular Concentration of a Methyl Donor Co-factor Hosts An important aspect of the invention is the host for expressing DNA from a restriction enzyme source organism. Practically any organism can be used in the invention. Suitable hosts thus include *E. coli*, *B. subtilis*, yeast, insect and mammalian cells, to name just a few.

Preferred hosts of the invention are not affected by low cellular concentrations of a methyl donor co-factor in a way that precludes detecting the presence of a cloned restriction endonuclease or methyltransferase.

For instance, preferred hosts do not express an endogenous methyltransferase activity that adversely affects cellular growth in the presence of low cellular concentrations of the methyl donor co-factor. Thus, for example, preferred *E. coli* hosts are dam. *E. coli* cells of this genotype do not express the *E. coli* DNA adenine methyltransferase, which regulates DNA replication. This enzyme methylates newly replicated DNA. Low cellular concentrations of the methyl donor co-factor S-adenosyl-L-methionine inhibit the activity of the enzyme leading to the production in the cell of hemimethylated DNA in the host. Hemimethylated DNA is not well replicated by *E. coli*. Therefore, low cellular concentration of S-adenosyl-L-methionine inhibits cell growth, which can interfere with some assays useful in the invention to detect the presence of the cloned restriction endonuclease. Thus, *E. coli* hosts for use in the invention are preferably dam. The dam system and *E. coli* mutants in this system are described in Landoulsi et al., *Cell* 63: 1053 (1990), for instance, herein incorporated by reference in its entirety.

Also preferred in the invention are hosts that do not cleave methylated DNA. A variety of methyl-dependent restriction-modification systems have been described in which cleavage by the endonuclease occurs only where the recognition sequence has been methylated by the cognate methyltransferase. When DNA encoding a heterologous methyltransferase is expressed in a host of this type the cloned methyltransferase may cause DNA damage by fortuitously methylating host DNA at cleavage sites of the methylation-dependent endonuclease. Damage arising from this circumstance can cause cell death, interfere with cell growth, and interfere in other ways with detecting a cloned restriction endonuclease by an effect of DNA damage. Therefore, preferred hosts for identifying cloned restriction endonuclease and methyltransferase genes do not have active systems of this type. These systems are well known to those of skill in the art and have been described, for instance, in Raleigh et al., *Proc. Nat'l Acad. Sci., U.S.A.* 83: 9070 (1986), which is herein incorporated by reference in its entirety.

For example, systems of this type have been described in *E. coli*. Genotypically the methylation dependent enzymes are referred to as mcrA, mcrB, mcrC, mcrD, mcrE, mcrF and mrr, as described in Raleigh et al., *J. Bac.* 173: 2707 (1991), for instance, also herein incorporated by reference in its entirety. Accordingly, *E. coli* deficient in mcrA, mcrB, mcrC, mcrD, mcrE, mcrF and mrr are preferred *E. coli* hosts.

In embodiments of the invention that detect a cloned restriction endonuclease by an effect of double-stranded DNA damage, host cells preferable do not repair such damage, as by the action of a ligase, in such a way that repair interferes with detecting the presence of the cloned gene.

In *E. coli*, repair of this type is mediated by the genes lig4 and lig7, which encode DNA ligases. To prevent repair of double strand breaks that will interfere with detecting a cloned restriction endonuclease gene expressed in *E. coli* host, preferred *E. coli* host for use in the invention include lig4, lig7 and lig4 and lig7 deficient stains of *E. coli*. Mutations in these genes are described in Konrad et al., *J. Mol. Biol.* 77:519 (1973) and Gottesman et al., *J. Mol. Biol.* 77:531 (1973), for example, herein incorporated by reference in their entirety.

Use of host stains characterized by these mutations will facilitate the effect on cell growth by a cloned restriction enzyme, facilitating detection of clones that contain the enzyme by a growth inhibiting or lethal effect on the host cells. Such effects readily may be detected by following optical density of cultures during growth or by assaying ability to form colonies on plates. Methods for assaying cell growth and viability suitable for use in this regard are well known to those of skill in the art and are described in many widely available laboratory manuals, such as Sambrook (1989), supra.

Methyl donor co-factors

Any methyl donor co-factor of a DNA methyltransferase may be used in the invention. The most common co-factor or methyltransferase is S-adenosyl-L-methionine, which is most highly preferred for use in this invention. Another methyl donor co-factor useful in the invention is cobalamin.

Modulating the intracellular concentration of methyl donor co-factor

A variety of methods can be used to modulate the cellular concentration of a methyl donor co-factor in accordance with the invention. Although the following discussion related to S-adenosyl-L-methionine, similar considerations and approaches are applicable to other factors.

Hosts useful in the preferred embodiments of the invention can be used to modulate the cellular concentration of S-adenosyl-L-methionine effective to alter the activity of a methyltransferase in protecting DNA from damage by a cloned restriction endonuclease.

One general approach to modulating the cellular concentration of S-adenosyl-L-methionine is to control the activity of an enzyme that effects S-adenosyl-L-methionine synthesis or degradation in the cell. A variety of such enzymes are known and may be used in the invention. FIG. 1 is a diagram which highlights enzymes from several organisms that can affect the intracellular concentration of S-adenosyl-L-methionine.

The activity of enzymes that affect the cellular concentration of S-adenosyl-L-methionine, such as those in FIGS. 1A, 2B and 2C, are charts can be controlled in a variety of ways to detect the presence of a cloned restriction endonuclease or methyltransferase in accordance with the present invention.

For instance, in certain preferred embodiments of the invention, cells can be cultivated in the presence of substances that inhibit or increase the activity of enzymes that affect cellular concentrations of S-adenosyl-L-methionine.

In other preferred embodiments the cellular concentration of S-adenosyl-L-methionine is controlled by altering growth temperature to control a temperature sensitive enzyme of S-adenosyl-L-methionine metabolism. The enzyme may be expressed by an endogenous gene or it may be expressed by an exogenously derived gene. Methods for creating temperature sensitive mutations and isolating the mutated genes are well known to those of skill in the art. Sambrook (1989), supra, illustrates some methods useful in this regard.

In another preferred embodiment of the invention the cellular concentration of S-adenosyl-L-methionine is regulated by the expression of an exogenously derived gene that encodes an enzyme of S-adenosyl-L-methionine metabolism. Generally, in these embodiments the gene will be operably linked to an inducible transcription control region suitable to control the amount and activity of the enzyme in the host. (A promoter, as referred to herein, is a transcription control region).

Methods for isolating genes of S-adenosyl-L-methionine metabolism useful in this aspect of the invention are well known to those of skill in the art. For instance, methods for cloning and expressing genes in accordance with this aspect of the invention are described in standard lab manuals such as Sambrook (1989), supra. Likewise, a wide variety of vectors and inducible transcription control regions suitable for use in this aspect of the invention are widely available and well known to those skilled in the art. An illustrative selection of vectors for inducible expression of cloned genes is provided in Sambrook (1989), supra.

Preferred promoters for use in accordance with the invention are tightly controlled inducible promoters that exhibit inducer dose dependent induction. With promoters of this type expression of enzymes that affect the cellular concentration of S-adenosyl-L-methionine can be adjusted to the optimum balance of the deleterious effect of low S-adenosyl-L-methionine on the host and sensitivity to the effects of DNA damage by a cloned restriction endonuclease. Particularly preferred promoters include the E. coli lac, mac, trp, tac, and trc promoters and the Tn10 tet promoter.

The Tn10 tet promoter is especially highly preferred since it has been shown to have very stringent regulation of transcription and it can be dose-dependently controlled by the inducer chlortetracycline.

Figure 1B:
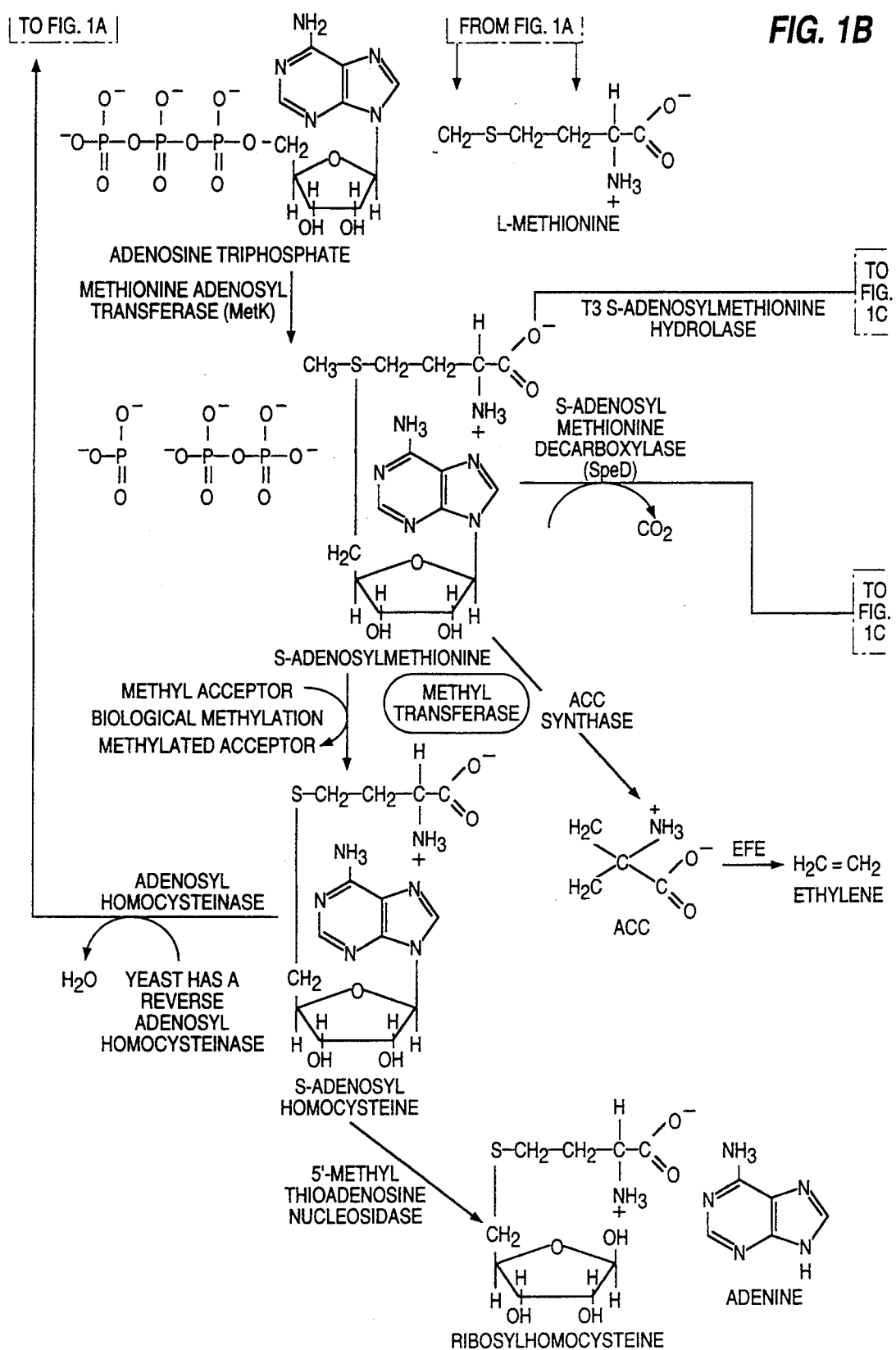

A number of enzymes that can be employed to control the cellular concentration of S-adenosyl-L-methionine in accordance with the invention are shown in FIGS. 1A, 1B and 2C. A preferred class of suitable enzymes are S-adenosyl-L-methionine synthetases. Another preferred class of enzymes are those that degrade S-adenosyl-L-methionine.

Highly preferred among those enzymes that affect S-adenosyl-L-methionine synthesis are the S-adenosylmethionine synthetases, particularly the E. coli metK gene product.

Highly preferred among enzymes that degrade S-adenosyl-L-methionine are the enzymes S-adenosyl-L-methionine hydrolase, aminocyclopropane-1-carboxylic acid synthase and S-adenosyl-L-methionine decarboxylase. Particularly preferred among these enzymes is the T3 S-adenosyl-L-methionine hydrolase (also called SAMase) and the S-adenosyl-L-methionine decarboxylase product of the E. coli Sped gene.

The T3 S-adenosyl-L-methionine hydrolase represents a very highly preferred class of enzymes for use in accordance with the invention. These are enzymes expressed by invasive genetic elements such as phage, plasmids and F factors that naturally function to reduce the levels S-adenosyl-L-methionine in cells to protect the element from the cellular restriction system.

Figure 1C:
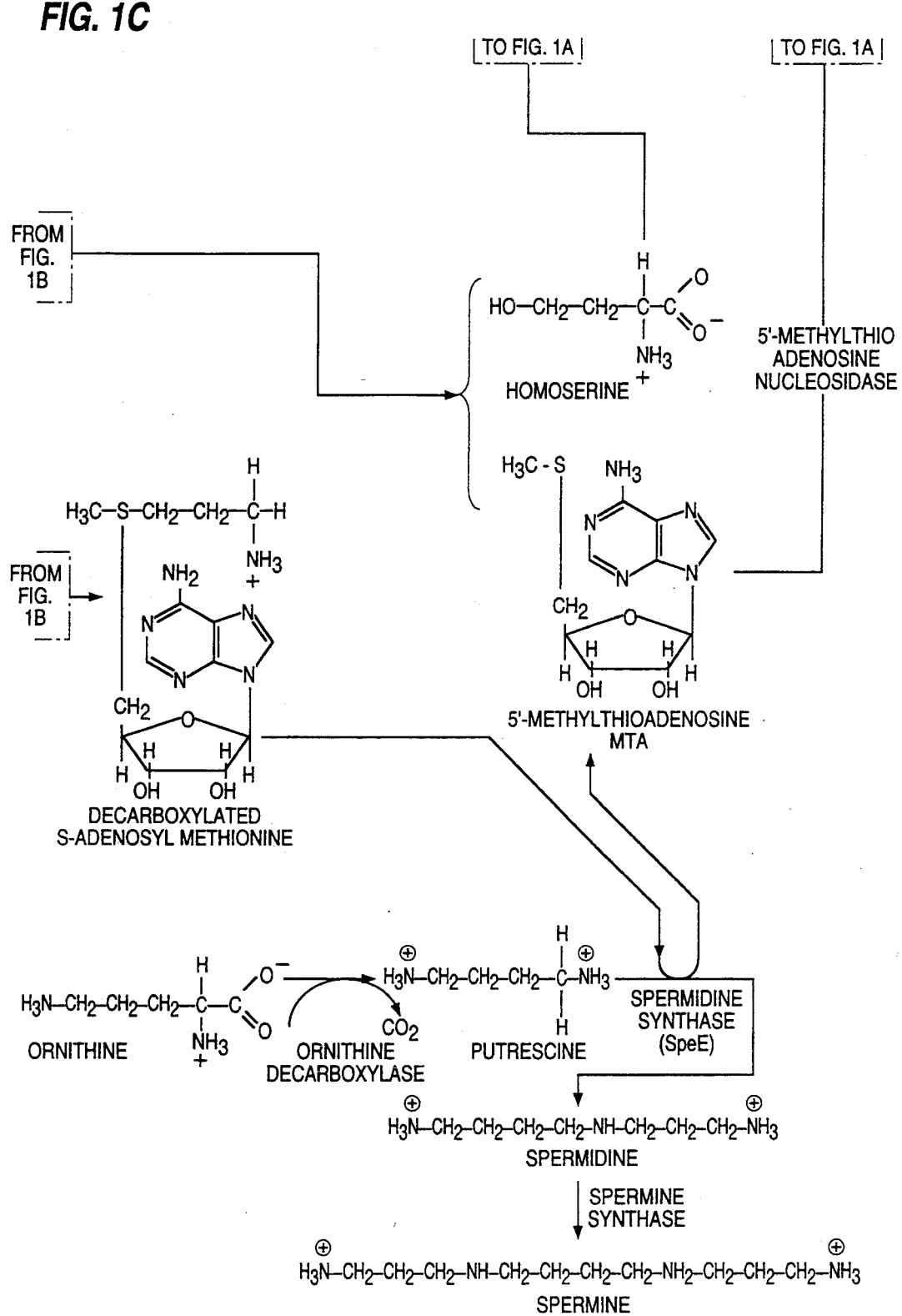

As shown in FIGS. 1A, 1B and 1C S-adenosyl-methionine synthetase plays a pivotal role in S-adenosyl-L-methionine metabolism and its activity substantially affects S-adenosyl-L-methionine concentration in the cell.

One method for regulating S-adenosylmethionine synthetase in a host cell is by growing cells in the presence of an inhibitor of the enzyme, as set forth more generally above. Inhibitors can be used to inhibit the enzyme whether it is expressed by an endogenous gene or an exogenously derived gene. Suitable inhibitors include but are not limited to L-2-amino-4-methoxy-cis-but-3-enoic acid, selenomethionine, cycloleucine and 2-aminobicyclo[2.1.1]hexane-2-carboxylic acid. The inhibitors can be used in accordance with standard methods well known to those of skill in the art, as described in Sufrin et al., B.B.R.C. 106:251 (1982) and Porter et al., B.B.R.C. 122:350 (1984), which are herein incorporated by reference in their entirety.

Preferred embodiments of this aspect of the invention, therefore, inducibly express the E. coli metK gene. The gene has been cloned. A temperature-sensitive mutant of the cloned gene has been generated. And, furthermore, a host cell strain has been derived in which the temperature sensitive gene has replaced the endogenous gene. This work is described in Hafner et al., J. Bac. 132:832 (1977) and Satishchandran et al., J. Bac., 172 4489 (1990), herein incorporated by reference in their entirety.

However, the mutant strains reported by Hafner and Satishchandran were not stable, apparently because metK expression was enfeebled even at the permissive temperature and it is essential to viability. Such strains may be used to provide a particularly low background of S-adenosylmethionine synthetase expression when used in conjunction with a vector for inducible expression of exogenously derived gene for S-adenosylmethionine synthetase. Thus, in embodiments of this type control of metK by an inducible promoter is preferred.

It will be appreciated by those of skill in the art that similar methods can be used to control the intracellular concentration of any methyl donor cofactor by controlling the activity or expression of an enzyme.

Another enzyme that can have a substantial effect on the cellular concentration of S-adenosyl-L-methionine is the S-adenosyl-L-methionine hydrolase of bacteriophage T3. This enzyme cleaves S-adenosyl-L-methionine to yield homoserine and methylthioadenosine, as shown in FIGS. 1A, 1B and 1C. In fact, the natural role of this enzyme is to reduce S-adenosyl-L-methionine levels in host cells during T3 infection. In this, it is one of a class of enzymes ideally suited to use in the accordance with the present invention. The T3 hydrolase gene has been cloned and characterized, as described in Hughes et al., J. Bac. 169: 3625 (1987), which is herein incorporated by reference in its entirety. Moreover, it is well characterized.

Detecting the Effect of Intracellular Concentration of a Methyl Donor Co-factor

It will be appreciated by those of skill in the art that any methyl donor cofactor may be used in the invention in the same manner as described below for S-adenosyl-L-methionine.

In a general aspect of the invention, as described above, the presence of a gene encoding a restriction endonuclease is detected by assessing cellular DNA damage when the intracellular concentration of S-adenosyl-L-methionine is changed. When the concentration is high, methyltransferase activity will prevent DNA damage by a cognate restriction endonuclease. In low concentrations of S-adenosyl-L-methionine, the host DNA will be damaged by the activity of the endonuclease. The presence of a gene encoding a restriction endonuclease is determined in a colony or culture by assessing double strand DNA breaks when cellular concentrations of S-adenosyl-L-methionine are low.

DNA damage induced in a host cell by a cloned restriction endonuclease can be determined in accordance with the invention by a variety of methods well known to those of skill in the art. Such methods include but are not limited to methods for detecting an inhibition of cell growth and methods for determining the activity of a reporter gene controlled by a promoter sensitive to the cellular effects of DNA damage caused by the restriction endonuclease. Such reporter genes may be endogenous or exogenously derived and they may be under the control of their own promoter or another promoter.

Accordingly, practically any methods for determining cell growth in a culture can be used to determine the inhibiting effect of a restriction endonuclease in low S-adenosyl-L-methionine concentration in cells in liquid culture. Among the common methods for measuring growth in bacterial cultures that may be used to this end is determining optical density in the range of 500 and 700 nm. Another common method useful in this aspect of the invention is to compare the growth of corresponding colonies on replica plates.

The presence of a gene encoding a restriction enzyme also may be determined by detecting proteins induced by DNA damage. As one example of this approach, double stand cleavage is detected by an increase in the cellular concentration of RecA protein. A preferred method to assay RecA levels in colonies in situ is immunogical screening using a RecA specific antibody. Methods for screening colony and plaque lifts with antibodies are described in Sambrook (1989), supra, among others.

Alternatively, restriction endonuclease activity can be determined in accordance with the invention by the effect of DNA damage on the expression of a gene operably linked to a promoter that is responsive to a cellular effect of the damage. Promoters that are effected by double-strand breaks in DNA are preferred in this aspect of the invention. Among such promoters, the SOS sensitive promoters are particularly preferred.

E. coli SOS-sensitive transcriptional regulatory regions that are sensitive to effects engendered by double-strand DNA breaks and are suitable for use in the invention include but are not limited to promoters of the dinA, dinB, dinD, dinF, dinG, dinH, dinR, dinY, DDB, DRP, gadd153, PHR1, and RAD2 genes. Among these promoters the promoter of the dinD gene is particularly preferred because it is highly induced by DNA damage.

A wide variety of reporter genes are well known to those of skill in the art. Any gene for a reporter activity compatible with a host may be used in this aspect of the invention. Reporter genes for determining the activity of a transcription unit are described in many laboratory manuals, including Sambrook (1989), supra.

Preferred reporter genes are those that encode beta-galactosidase, horseradish peroxidase, alkaline phosphatase, luciferase, chloramphenicol acetyltransferase, B-glucuronidase, glutathionine S-transferase and cellulase. However, those of skill will appreciate that this list is merely illustrative and other reporter genes may be used in the invention.

In a particularly preferred embodiment of this aspect of the invention, the beta-galactosidase structural gene is operably linked to the dinD promoter, and beta-galactosidase expression thereby is controlled by DNA damage in a host cell. A host cell line comprising a dinD-beta-galactosidase fusion gene suitable for use in this aspect of the invention is GUBCE-1, described in EXAMPLE 3 below. In this cell line, the dinD-beta-galactosidase fusion gene is stably integrated in the host genome. Those of skill will appreciate that GUBCE-1 and similar cell lines can be used with a wide variety of cloning vehicles.

Hosts deficient in the genes that repair DNA damage caused by restriction endonucleases are preferred hosts for use in the invention, as described above. Such hosts are more sensitive to the deleterious effect of the restriction endonuclease. In E. coli, host cells deficient in lig4 or lig7 or both are preferred for use in the invention. Because they are unable to repair DNA damage, growth of these cells is more sensitive to the double-strand DNA breaks made by the restriction endonucleases. Moreover, deficiencies in these genes also can augment induction of the SOS response by restriction endonuclease-mediated DNA damage.

Another preferred method for detecting the presence of a restriction endonuclease is by complementation. In this method, a gene that encodes a protein essential for production of viable phage is placed under the control of an SOS-sensitive promoter in a host cell. The cells are infected with bacteriophage that are deficient in the gene controlled by the SOS promoter. Viable bacteriophage are produced only upon SOS-induced production of the essential protein. A variety of trans-complementation designs can be used in this aspect of the invention.

In accordance with this embodiment of the invention, when DNA from a source organism is cloned directly into the deficient bacteriophage, viable phage from the transduced cells contain the gene encoding the restriction endonuclease. Thus, the method provides direct selection of clones encoding restriction endonucleases.

The well-characterized bacteriophage M13 and its derivatives, such as those of the commonly used M13mp-series vectors, are preferred in the invention for use in a selection method of this type. Preferably the M13 is defective in gene III or gene VIII or both.

Many deficient bacteriophage strains suitable for use in this aspect of the invention have been described and are well known to those of skill in the art. Moreover, those of skill will be familiar with a variety of methods for creating mutations in vivo and in vitro in bacteriophage DNA for use in accordance with this aspect of the invention. Furthermore, methods for collecting bacteriophage from cells and for making DNA from the phage also are well known. A variety of such methods are well described in Sambrook (1989), supra, as well as many other widely available laboratory manuals.

Two Step Cloning

Sometimes methyltransferase expression from the endogenous promoter may not completely protect host DNA against the activity of a cloned restriction endonuclease. This may occur, for instance, when the methyltransferase promoter inherently is inefficient, when it is expressed inefficiently by the transcription proteins of the transformation host, when endogenous transcription control signals of the methyltransferase gene interfere with efficient expression, or for other reasons. It has been suggested that the BamHI and DdeI restriction systems pose this problem, as described in U.S. Pat. No. 5,098,839 and in Lunnen et al., Gene 74:25 (1988)

It will be advantageous when this problem is encountered to clone the gene encoding the methyltransferase separately from the gene for the restriction endonuclease. Then the cloned methyltransferase can be introduced into a host to provide immunity to the endonuclease. Subsequently, a gene encoding the restriction endonuclease can be introduced into the immune cells and detected by the methods described hereinabove.

In a preferred embodiment of this aspect of the invention the methyltransferase and the restriction endonuclease are introduced into the host on DNAs with mutually compatible replicons. In a particularly preferred embodiment the replicons are the ColE1 and p15 replicons.

The present invention is further described by reference to the following, illustrative examples.

EXAMPLE 1

Construction of a vector for controlling the concentration of S-adenosyl-L-methionine in a host cell The cloning methods in the experiments in the following example are conventional methods well known to those of skill in the art such as those described in, for instance, Sambrook et al. (1989) supra.

pCF3 was used as a convenient source of the TN10 tet region as described in Takiff et al., J. Bac. 171: 2581 (1989). pHF1UC was used as a convenient source of the bacteriophage T3 S-adenosyl-L-methionine hydrolase gene, as described in Hughes et al., J. Bac. 169: 3625

(1987) and Hughes et al., *Nuc. Acids Res.* 15:717 (1987). The convenient cloning vector which was used in this example, pTZ19R, is described in Mead et al., *Prot. Eng.*, 1: 67 (1986). Takiff(1989), Hughes (1987) and Hughes (1987), supra are herein incorporated by reference in their entirety.

A 2.5 kb fragment containing the TN10 tet region was removed from pCF3 by digestion with BamHI and EcoRI. A 1.0 kb fragment containing the T3 hydrolase gene was isolated from pHF1UC by digestion with EcoR1 and HindIII. Following electrophoresis through agarose the fragments were recovered by ethanol precipitation from agarase liquified slices of the gel.

The vector was cut with BamHI and HindIII, dephosphorylated using a heat sensitive alkaline phosphatase, incubated at 65° C., electrophoresed through agarose and the 2.8 kb linearized vector was isolated from a slice of the gel using agarase followed by ethanol precipitation.

The three gel purified DNA fragments were ligated together in a single reaction by overnight incubation at 14° C. with T4 DNA ligase.

Following ligation the mixture was incubated for 20 minutes on ice with competent MC1061 dam−/F′IQ cells, then heat-shocked for 90 seconds at 42° C., incubated on ice for 2 minutes and then spread on 2YT plates containing ampicillin and kanamycin.

After overnight incubation at 37° C., 20 of the colonies on the plates were expanded in 5 ml liquid cultures. The cells were spun out of the cultures and DNA was isolated from the pellets by SDS/alkaline lysis followed by KOAc-isopropanol precipitation.

The DNA was analyzed by restriction digestion and gel electrophoresis to confirm the size and proper arrangement of the tet and T3-derived fragments in the vectors. Further confirmation of the structure of the DNA was obtained by culturing a transformed host strain and measuring the induction of T3 S-adenosyl-L-methionine hydrolase activity upon induction of the TN10 promoter by chlortetracycline. The plasmid from this strain was called pGUBC-2000.

pGUBC-2000 was a useful intermediate vector but contained a well-known part of the TN10 tet region that impedes cell growth when it is expressed, as described in Allard et al., *J. Biol. Chem.* 267: 17809 (1992), herein incorporated by reference in its entirety. This region was removed from the vector by digestion with SmaI and HpaI. Part of the deleterious sequence was removed in the dispensable 1.1 kb fragment resulting from this digestion. The 5.5 kb fragment containing the rest of the vector was circularized by ligation using T4 ligase, transformed into host cells, spread and plate cultured overnight and the colonies expanded as described above. DNA was isolated from the cultures characterized by restriction mapping and enzyme induction also as described above.

The 5.5 kb vector was digested with Esp3I and NcoI and then treated with T4 DNA polymerase to fill in the overhanging ends. The 800 bp fragment produced by the digestion was not used any further. The 4.7 kb fragment produced by the digestion was recovered from the gel and circularized using T4 DNA ligase by the methods described above. The ligated DNA was transformed into host cells, cultured, reisolated and characterized also using the same methods as before. This plasmid was called pGUBC-2060. As shown in FIG. 2, the TN10-T3-derived region in this plasmid is the same as in pGUBC-2080, described below.

To facilitate the use of this plasmid to express the hydrolase in a host containing additional plasmids, the TN10-T3-derived region from pGUBC-2060 was transferred into a vector controlled by the p15A replicon.

As is well known plasmids containing this replicon stably persist in cells alongside plasmids controlled by the ColEI replicon, avoiding the plasmid incompatibily that occurs when two different plasmids controlled by the same replicon are cultured together in the same cell. Incompatibilty quickly results in the loss of one plasmid or the other from the culture. Incompatibility is described in Chabbert et al., *J. Bac.* 112: 666 (1972), for example, herein incorporated by reference in its entirety.

A well known vector controlled by the p15A replicon, pACYC184, was conveniently employed as a p15A vector for the TN10-T3-derived segment of pGUBC-2060. pACYC184 is described in Rose, *Nuc. Acids Res.* 16: 355 (1988), herein incorporated by reference in its entirety. pACYC184, accession number 37033, has been deposited by S. N. Cohen with the ATCC. The vector was cultured and the DNA purified as described above and characterized by restriction mapping. The pACYC184 DNA was cut with EcoRV, dephosphoylated, and gel purified as described above. pGUBC-2060 was digested with PvuII and a 1.7 kb fragment containing the TN10-T3-derived region was purified from the gel after electrophoresis as described above. The gel-purified vector and fragment containing the TN10-T3-derived region were ligated, transformed and cultured as described above. DNA was isolated from expanded colonies and characterized also as described above. The resulting plasmid was designated pGUBC-2080. The restriction map of the TN10-T3-derived region in pGUBC-2080 is shown in FIG. 2.

EXAMPLE 2

S-adenosyl-L-methionine hydrolase expression can modulate DNA methylation by decreasing the activity of a cloned methyltransferase.

To demonstrate that S-adenosyl-L-methionine hydrolase could be used to control cellular DNA methylation pGUBC-2080 was introduced into *E. coli* 3055 cells (described below) together with pMBamHII, a plasmid that constitutively expresses a BamHII methyltransferase. pMBamHII is described in Connaughton et al., *Nuc. Acids Res.* 18:4002 (1990).

The transformed cells were cultivated in 2YT media as described above, in the presence of 0, 0.25, 0.50 or 0.75 micrograms per mL of chlortetracycline to induce expression of the T3 S-adenosyl-L-methionine hydrolase by the TN10 tet promoter. The effect of chlortetracycline-induced hydrolase expression on BamHI methyltransferase activity was determined by measuring the ability of BamHI to cleave plasmid DNA isolated from the cultured cells.

Figure 3:
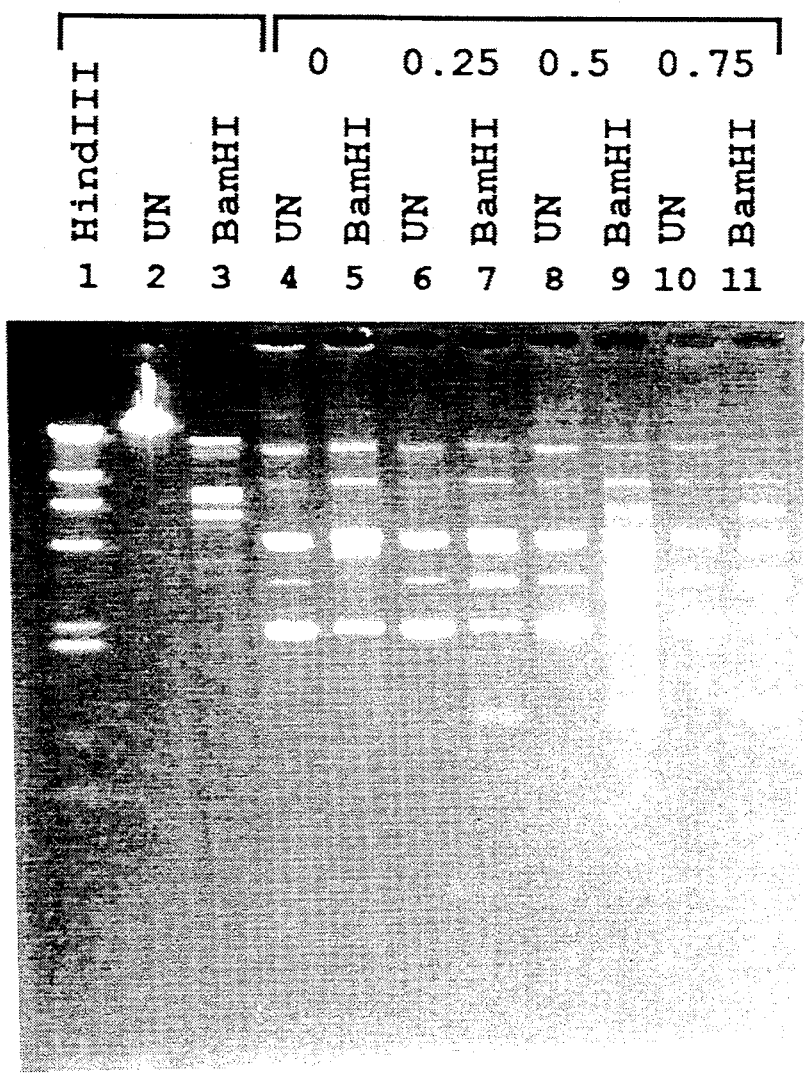
FIG. 3 is a photograph of DNA in an agarose gel showing that the expression of S-adenosyl-L-methionine hydrolase induced by chlortetracycline inhibits methylation by BamHII methyltransferase, as described in EXAMPLE 2 (un=uncut).

FIG. 3 shows the results of an experiment of this type. Lanes 1–3 contain lambda DNA-derived size markers, as indicated above each lane. Lanes 4 and 5, respectively, show control and BamHI digested pGUBC-2080 and pMBamHII DNA from cells cultured in the absence of chlortetracycline. Lanes 6 and 7, respectively, show uncut and BamHI cut pGUBC-2080 and pMBamHII DNA from cells cultured in 0.25 micrograms per mL of chlortetracycline. Lanes 8 and 9, respectively, show control and BamHI digested pGUBC-2080 and pMBamHII DNA from cells cultured in 0.50 micrograms per mL of chlortetracycline.

Lanes 10 and 11, respectively, show control and BamHI digested pGUBC-2080 and MBamHII DNA from cells cultured in 0.75 micrograms per mL of chlortetracycline.

Since the copy number of pGUBC-2080 in these cells is significantly lower than the copy number of pMBamHII, the most significant indicator of DNA methylation was a 1 kb BamHI fragment arising from unmethylated pMBamHII DNA. The fragment can be clearly discerned in the lower portion of the gel below the other predominant digestion products. The fragment is not seen in the BamHI digest of the plasmid DNA from cells cultured in the absence of chlortetracycline. The obvious presence of the fragment in the BamHI digests of the DNAs from all cells cultivated in the presence of chlortetracycline thus clearly shows that hydrolase induction inhibits BamHII-mediated DNA methylation.

EXAMPLE 3

Construction of a dam$^-$ E. coli strain that expresses $\beta$-galactosidase in response to DNA damage.

In accordance with the foregoing discussion an E. coli strain was constructed which provides a convenient colorimetric assay for cellular DNA damage. It is well known that the dam methyltransferase inhibits plasmid and host cell replication by producing hemimethylated DNA, as described in Zinder et al., Cell 20: 1071 (1987). To avoid this problem the stain was constructed from a dam$^-$ strain of E. coli. The experiments in this example employed the dam$^-$ E. coli strain 3055, which is a dam$^-$ derivative of the well known and readily available E. coli strain MC1061. The method used to make 3055 from MC1061 are well known to those of skill and readily can be employed to make dam$^-$ derivatives not only of MC1061 but practically any other strain of E. coli. MC1061 has been deposited in the ATCC by Hoffman LaRoche under accession number 53338.

The JH139 strain of E. coli contains a dinD $\beta$-galactosidase fusion in which the dinD promoter operator controls expression of $\beta$-galactosidase, as described in Heitman et al., Gene 103: 1 (1991), herein incorporated by reference in its entirety. Also as described in Heitman, the same fusion contains a kanamycin resistance gene. JH139 thus was a particularly convenient source of an SOS-inducible $\beta$-galactosidase gene to indicate cellular DNA damage by a restriction endonuclease. Of course, many other constructs might be employed for this purpose, as described above.

The SOS-$\beta$-galactosidase fusion was isolated from JH139 and introduced into 3055 by P1 mediated transduction using well known standard methods as described, for instance, in J. H. Miller, EXPERIMENTS IN MOLECULAR GENETICS, Cold Spring Harbor Laboratory Press, Cold Spring Harbor, N.Y. (1972) the entirety of which is herein incorporated by reference. JH139 cells were mixed with P1 transducing phage at an moi very roughly of 0.01, spread on a petri plate and incubated at 37° C. overnight. P1 phage were collected from the plate lysate by incubating the plate with phage buffer for several hours at room ambient temperature. The buffer was collected, a drop of chloroform was added to kill any remaining viable cells, the solution was cleared of particulates by low speed centrifugation, and the supernatant, P1::JH139 phage stock, was used to transduce the dinD-$\beta$-galactosidase gene into 3055 cells.

3055 cells grown in medium containing 5 mM CaCl$_2$ were incubated with P1::JH139 phage as above and plated on kanamycin. Kanamycin resistance indicated the presence of the dinD-$\beta$-galactosidase fusion. The well known inducer of DNA damage, mitomycin C was used to test induction of $\beta$-galactosidase by dinD. Cells were cultivated in liquid media in 2YT broth containing 1 microgram per mL for four hours at 37° C. under otherwise standard conditions. Cells were pelleted and then assayed for $\beta$-galactosidase activity as described in Miller supra.

Briefly, the cells were washed and resuspended in Z buffer and then lysed by adding SDS to a final concentration of 0.025% and a drop of chloroform. (Z buffer is 0.06M disodium phosphate, 0.04M sodium dihydrogen phosphate, 0.01M potassium chloride, 0.001M magnesium sulfate, 0.05M $\beta$-mercaptoethanol, pH 7.0, as described in Miller supra.) ONPG was added to a final concentration of about 666 micrograms per mL and the lysate was incubated at 28° C. (ONPG is an abbreviation for the colorigenic $\beta$-galactosidase substrate o-nitrophenyl-$\beta$-D-galactoside.) The reaction was terminated by addition of sodium carbonate buffer. The yellow reaction product, which may be quantitated by optical absorption at 420 nm, indicated the production of $\beta$-galactosidase in response to mitomycin C. The strains likely to be most efficacious for cloning restriction enzymes were identified by efficient production of the yellow ONPG reaction product.

pGUBC-2080 was introduced into a stain that showed a 20-fold induction of $\beta$-galactosidase in response to mitomycin C. The strain was designated GUBCE-1. pGUBC-2080 was transformed into GUBCE-1 by conventional methods as described above and the strain resulting from the transformation was designated GUBCE-1/pGUBC-2080.

EXAMPLE 4

Induction of $\beta$-galactosidase in GUBCE-1/pGUBC-2080 by expression of a heterologous restriction enzyme in the presence of high and low levels of intracellular S-adenosyl-L-methionine The affect of intracellular S-adenosyl-Lmethionine on $\beta$-galactosidase induction by DNA damage by a restriction endonuclease was assessed by expressing a cloned EcoRI gene in GUBCE-1/pGUBC-2080. To this end pRI13, which constitutively expresses the EcoR1 endonuclease and the EcoR1 methyltransferase, and is under the control of the ColE1 replicon, was introduced into GUBCE-1/pGUBC-2080. Transformants of this type were designated GUBCE-1/pGUBC-2080/pRI13. Control cells transformed with pBR322 were produced in like manner. These cells were designated GUBCE-1/pGUBC-2080/pBR322.

GUBCE-1/pGUBC-2080/pRI13 cells were cultured in 2YT broth containing kanamycin, ampicillin, chloramphenicol and several concentrations of chlortetracycline. After four hours of growth at 37° C. under standard conditions the cells were collected and treated as described above to determine the production of $\beta$-galactosidase activity in response to the varying concentration of chlortetracycline and the intracellular expression of the EcoRI endonuclease and methyltransferase.

In 0.02 microgram per mL chlortetracycline, GUBCE-1/pGUBC-2080/pRI13 cells expressed 100% more $\beta$-galactosidase than control GUBCE-1/pGUBC-2080/pBR322 cells. This showed that S-adenosyl-L-methionine hydrolase activity induced by chlortetracycline was effective to modulate a detectable effect of a restriction enzyme on cellular DNA.

EXAMPLE 5

Cloning the NotI restriction endonuclease

Nocardia otitis-caviarum is obtained from the ATCC (accession number 14630) and is cultured by standard methods to obtain enough DNA to prepare a representative genomic library for expression in GUBCE-1/pGUBC-2080. Procedure that involve viable Nocardia cells in any amount are carried out in a P3 facility. DNA is prepared from an SDS/alkaline lysate of the cells by methods described above as set forth in Sambrook (1989), supra. The Nocardia DNA is partially cleaved by HaeIII and AluI. The DNA then is methylated by EcoRI methyltransferase. The methylated DNA is then ligated to oligonucleotide linkers containing an EcoRI site. The ligation product is cleaved with EcoRI. The EcoRI fragments are size fractionated by agarose gel electrophoresis. Fragments of 5 to 10 kb are isolated from the gel by methods described above. The EcoRI fragments are ligated to EcoRI-cleaved and dephosphorylated pBR322. The ligation products are transformed into GUBCE-1/pGUBC-2080. The transformed cells are titered.

50 aliquots each containing about 500 cfu are amplified in 2YT media containing kanamycin, ampicillin and chloramphenicol. The amplified cultures are titered. Aliquots containing about 500 cfu from each culture are cultivated in 2YT medium containing kanamycin, ampicillin, chloramphenicol and chlortetracycline. Otherwise identical aliquots are cultured under the same conditions without chlortetracycline. The cells are processed and β-galactosidase activity is determined using ONPG as described above. The aliquot producing the largest difference in absorption at 420 nm between growth in the presence and absence of chlortetracycline is subjected to further analysis.

Approximately 500 cfus from the selected aliquot is spread on plates at low density and cultured to produce isolated colonies. A portion of each colony is combined with 9 others in 2YT/amp/kan/cam media and the 50 cultures are amplified by overnight growth. A portion of each culture is analyzed for β-galactosidase activity as described before. The pool exhibiting the greatest induction by chlortetracycline is subjected to further analysis using the same methods as before.

The ten colonies in the selected pool are amplified independently in 2YT/kan/amp/cam as above and then portions of each culture are cultivated in 2YT/amp/kan/cam with and without chlortetracycline. β-galactosidase activity is assayed as before. One culture shows a significantly greater increase in absorbance at 420 nm than the others and it is subjected to further analysis.

Plasmid DNA is isolated from the cells of this clone and the DNA is analyzed by restriction mapping. The Nocardia DNA in the clone is isolated and sequenced. Several open reading frames are identified in the DNA sequence of the Nocardia-derived insert. Fragments containing the ORF are cloned into an expression vector operably linking the protein encoded by the ORF to a promoter in the expression vector. The expression constructs for each ORF separately are transformed into a host cell for expression. Reserving a portion of the transformed cells for future use, the cells are assayed for expression of the Nocardia endonuclease.

High levels of the enzyme are detected in cells expressing one of the ORFs, unambiguously identifying the NotI endonuclease gene. A gene encoding the cognate methyltransferase is identified by related methods.

What we claim is:

1. A method for cloning a gene encoding a restriction endonuclease comprising the steps of (i) modulating the cellular concentration of a methyl donor cofactor of a DNA methyltransferase and (ii) detecting the presence of the restriction endonuclease gene by an effect of said gene that differs before and after modulation of said concentration.

2. A method according to claim 1, wherein cellular DNA is protected from cleavage by said restriction endonuclease under a first growth condition and cellular DNA is cleaved detectably under a second growth condition.

3. A method according to claim 2, further comprising
   (a) introducing cloned DNAs comprising said gene into a cellular host;
   (b) propagating host cells in a replicable format under said first growth condition, then;
   (c) propagating a replicate of said host cells of step (b) under said second growth condition, and
   (d) detecting DNA encoding said gene by an effect of said gene that differs between said first and said second growth conditions.

4. A method according to claim 3, wherein said DNA is determined by comparing cell growth under said first and second growth conditions, decreased growth under said second growth condition indicating cells that contain said DNA encoding said restriction endonuclease.

5. A method according to claim 3, wherein a DNA cleavage-dependent transcription regulatory region controls expression of a detectable activity and said DNA encoding said gene is detected by the DNA cleavage-mediated induction or repression of said detectable activity.

6. A method according to claim 5, wherein said transcription regulatory region is a transcription regulatory region of an SOS responsive gene.

7. A method according to claim 6, wherein said SOS responsive gene is selected from the group consisting of dinA, dinB, dinD, dinF, dinG, dinH, dinR, dinY, DDb, DRP, gadd153, PHR1 and RAD2 genes.

8. A method according to claim 5, wherein said host cells are DNA ligase deficient cells.

9. A method according to claim 8, wherein said host cells are selected from the group consisting of lig4, lig7 and lig4/lig7 difficient cells.

10. A method according to claim 9, wherein said transcription regularly region is the transcription regulatory region of the E. coil dinD1 gene and said detectable activity is that of the enzyme β-galactosidase.

11. A method according to claim 5, wherein said detectable activity is the enzymatic activity of β-galactosidase, cellulase, luciferase, alkaline phosphatase, B-glucuronidase, glutathionine S-transferase or chloramphenicol acetyltransferase.

12. A method according to claim 3, wherein said host cells stably incorporate an exogenous DNA comprising a region that encodes a DNA methyltransferase operably linked to a transcription regulatory region whereby said methyltransferase expression in said cells is effective to protect the DNA of said cells from nucleolytic degradation by said restriction endonuclease.

13. A method according to claim 3, wherein said methyl donor cofactor of a DNA methyltransferase is selected from the group consisting of S-adenosyl-L-methionine and methylcobalamin.

14. A method according to claim 13, wherein said methyl donor cofactor of a DNA methyltransferase is S-adenosyl-L-methionine.

15. A method according to claim 14, wherein the concentration of S-adenosyl-L-methionine in said cells under said first and second growth conditions is controlled by a temperature sensitive enzyme of S-adenosyl-L-methionine metabolism or catabolism in said cells.

16. A method according to claim 15, wherein said host cell express a temperature sensitive S-adenosy-L-methoionine synthetase, the temperature in side first growth condition is permissive for S-adenosy-L-methoionine synthetase inactivitates said S-adenosyl-L-methinonine synthetase activity.

17. A method according to claim 13, wherein said second growth condition includes an inhibitor effective under said second growth condition specifically to inhibit S-adenposyl-L-methionine synthetase activity and said first growth condition does not inhibit and S-adenosyl-L-methionine synthetase activity.

18. A method according to claim 17, wherein said inhibitor is L-2-amino-4-methoxy-cis-but-3-enoic acid, selenomethionine, cycloleucine or 2-aminobicyclo[2.1.1]hexane-2-carboxylic acid.

19. A method according to claim 14, wherein the concentration of S-adenosyl-L-methionine in said cells under said first and second growth conditions is controlled by a protein which is encoded by a gene operably linked to an inducible transcription regulatory region, wherein transcription of said gene is repressed under said first growth conditions and induced under said second growth conditions.

20. A method according to claim 19, wherein said protein is an enzyme that degrades S-adenosyl-L-methonine.

21. A method according to claim 20, wherein said enzyme is S-adenosyl-L-methionine hydrolase, S-adenosyl-L-methonine decarboxylase or S-adenosyl-L-methionine methylthioadenosine-lyase.

22. A method according to claim 21, wherein said enzyme is the bacteriophage T3 S-adenosyl-L-methionine hydrolase.

23. A method according to claim 19, wherein said inducible transcriptional regulatory region is a repressible promoter, a repressor of said promoter is present in said cells under said first growth condition in an amount effective to repress said promoter, and said second growth condition includes an inducer of said repressor in an amount effective to induce synthesis of said protein by derepressing said promoter.

24. A method according to claim 23, wherein said protein is an enzyme that degrades S-adenosyl-L-methionine.

25. A method according to claim 24, wherein said protein is an S-adenosyl-L-methionine hydrolase, S-adenoysl-L-methionine decarboxylase or S-adenosyl-L-methionine methylthioadenosine-lyase.

26. A method according to claim 25, wherein said enzyme is bacteriophage T3 S-adenosyl-L-methionine hydrolase.

27. A method according to claim 26, wherein said inducible transcriptional regulatory region is the TN10 tetracycline promoter and said repressor is the TN10 tetracycline repressor.

28. A method according to claim 27, wherein said inducer is tetracycline or chlortetracycline.

29. A method according to claim 3, wherein said host is dam methyltransferase deficient.

30. A method according to claim 3, wherein said host does not restrict methylated DNA.

31. A method according to claim 30, wherein said host is an mcrA, mcrB, mcrC, mcrD, mcrE, mcrF or mrr deficient strain.

32. A host cell, comprising:
 (A) a first exogenously-derived inducible promoter not controlled by the cellular effects of DNA damage operably linked to a first exogenously-derived gene that encodes a protein for modulating the intracellular concentration of S-adenosyl-L-methionine, and
 (B) a second exogenously-derived promoter which is regulated by the cellular effects of restriction endonuclease-mediated DNA damage operably linked to a second exogenously-derived gene that encodes a reporter protein, wherein
 (C) inducing said first promoter modulates the intracellular concentration of S-adenosyl-L-methionine and restriction endonuclease-mediated DNA damage is determined by said reporter protein.

33. A host cell according to claim 32, wherein said cell is E. coli GUBCE-1.

34. A vector for propagating DNA in a host cell, comprising: an inducible promoter which is not controlled by the cellular effects of DNA damage operably linked to an exogenously derived gene that encodes a protein for modulating the intracellular concentration of S-adenosyl-L-methionine.

35. A vector according to claim 34, wherein said vector is pGUBC-2080.

36. An isolated, purified DNA comprising a region encoding a cognate methyltransferase and restriction endonuclease obtained by method comprising the steps of (i) modulating the cellular concenttration of a methyl donor cofactor of a DNA methyltransferase and (ii) detecting the presence of said region by an effect of said region that differs before and after modulation of said concentration.

37. An isolated, purified DNA according to claim 26, wherein in said method cellular DNA is protected from cleavage by said restriction endonuclease under a first growth condition and cellular DNA is cleaved detectably under a second growth condition.

38. An isolated, purified DNA according to claim 37, wherein said method further comprises:
 (a) introducing clone DNAs comprising said region into a cellular host;
 (b) progating host cells of step (a) in replicable format under said first growth condition, then;
 (c) propagating a replicate of said host cells of step (b) under said second growth condition, and
 (d) detecting DNA comprising said region said first and said second growth conditions.

39. An isolated, purified DNA according to claim 38, wherein said method said methyl donor cofactor is S-adenosyl-L-methionine.

40. An isolated, purified DNA according to claim 39, wherein in said method the concentration of S-adenosyl-L-methionine in said cells under said first and second growth conditions is determined by chlortetracycline induced expression of a bacteriophage T3 S-adenosyl-L-methionine hydrolase gene operably linked to a TN10 tetracycline promoter and the presence of a gene encoding a restriction endonuclease is determined by SOS-induced expression of a β-galactosidase gene operably linked to an E. coli dinD1 promoter.

* * * * *